United States Patent
Dey et al.

(10) Patent No.: US 11,382,617 B2
(45) Date of Patent: Jul. 12, 2022

(54) UNIVERSAL WINDING MACHINE FOR A MULTITUDE OF TRAY DESIGNS

(71) Applicant: Harro Höfliger Verpackungsmaschinen GmbH, Allmersbach im Tal (DE)

(72) Inventors: Clifford Dey, Allmersbach im Tal (DE); Ingmar Neff, Allmersbach im Tal (DE); Sven Brecht, Allmersbach im Tal (DE)

(73) Assignee: Harro Höfliger Verpackungsmaschinen GmbH, Allmersbach im Tal (DE)

( * ) Notice: Subject to any disclaimer, the term of this patent is extended or adjusted under 35 U.S.C. 154(b) by 471 days.

(21) Appl. No.: 16/564,106

(22) Filed: Sep. 9, 2019

(65) Prior Publication Data
US 2020/0078013 A1    Mar. 12, 2020

(30) Foreign Application Priority Data
Sep. 10, 2018   (EP) .................................. 18 193 349

(51) Int. Cl.
| | | |
|---|---|---|
| *A61B 17/06* | (2006.01) | |
| *B65B 63/04* | (2006.01) | |
| *B65B 19/34* | (2006.01) | |
| *B65B 35/10* | (2006.01) | |
| *A61B 17/00* | (2006.01) | |

(52) U.S. Cl.
CPC .. *A61B 17/06004* (2013.01); *A61B 17/06114* (2013.01); *B65B 19/34* (2013.01); *B65B 35/10* (2013.01); *B65B 63/04* (2013.01); *A61B 17/06133* (2013.01); *A61B 2017/00526* (2013.01); *A61B 2017/06147* (2013.01)

(58) Field of Classification Search
CPC ........ A61B 17/06004; A61B 17/06133; A61B 2017/00526; B65B 63/04
See application file for complete search history.

(56) References Cited

U.S. PATENT DOCUMENTS

| | | | |
|---|---|---|---|
| 5,473,810 A * | 12/1995 | Demarest | B65H 67/044 29/243.517 |
| 5,487,216 A | 1/1996 | Demarest et al. | |
| 5,660,024 A | 8/1997 | Ivanov et al. | |
| 5,661,954 A | 9/1997 | Ivanov et al. | |
| 5,664,404 A | 9/1997 | Ivanov et al. | |
| 5,788,062 A | 8/1998 | Cerwin et al. | |
| 5,920,482 A | 7/1999 | Demarest et al. | |

(Continued)

FOREIGN PATENT DOCUMENTS

| | | |
|---|---|---|
| EP | 0760227 A1 | 3/1997 |
| EP | 0676172 B1 | 8/1998 |
| EP | 3153117 A1 | 4/2017 |

*Primary Examiner* — Andrew M Tecco
(74) *Attorney, Agent, or Firm* — Smartpat PLC

(57) ABSTRACT

A suture attaching station attaches a needle and a suture to form a single combination. The setup of the crimping unit is facilitated by using an offline measuring fixture. The offline measuring fixture is calibrated by placing a precision gage block into the measuring fixture and then zeroing a digital measuring unit. The gage block is then replaced by the desired crimping die and the reading is noted as an offset for the servo drive of the suture attaching station. This offset is used to set the zero point of the crimping die centre.

2 Claims, 3 Drawing Sheets

(56) References Cited

U.S. PATENT DOCUMENTS

| | | | |
|---|---|---|---|
| 5,964,075 A | 10/1999 | Daniele et al. | |
| 5,970,686 A | 10/1999 | Demarest et al. | |
| 6,012,216 A * | 1/2000 | Esteves | B65B 67/1255 |
| | | | 29/788 |
| 6,014,851 A | 1/2000 | Daniele et al. | |
| 6,032,343 A * | 3/2000 | Blanch | G05B 19/4182 |
| | | | 53/118 |
| 6,081,981 A * | 7/2000 | Demarest | A61B 17/06004 |
| | | | 29/430 |
| 6,115,650 A | 9/2000 | Demarest et al. | |
| 6,463,719 B2 | 10/2002 | Dey et al. | |
| 6,804,937 B2 | 10/2004 | Dey et al. | |
| 6,807,796 B1 * | 10/2004 | Dey | A61B 17/06133 |
| | | | 53/430 |
| 2004/0177594 A1 | 9/2004 | Dey et al. | |
| 2010/0139351 A1 | 6/2010 | Bruhin | |
| 2014/0005676 A1 | 1/2014 | Shelton, I et al. | |
| 2016/0317148 A1 | 11/2016 | Martinez | |
| 2017/0174372 A1 | 6/2017 | Quinones | |
| 2019/0039769 A1 | 2/2019 | Dey et al. | |

* cited by examiner

UNIVERSAL WINDING MACHINE FOR A MULTITUDE OF TRAY DESIGNS

TECHNICAL FIELD

This invention relates to packages for surgical sutures and surgical needles, more particularly to equipment for attaching surgical sutures to needles and loading them into a winding machine.

BACKGROUND

Surgical needles and attached surgical sutures are well known in the art. Surgical needles and sutures are packaged in a variety of packages for delivery of the needles and sutures to the surgeon. The packages need to have a number of important characteristics, including ease of loading, ease of dispensing, and protection of the needle and the suture during handling, sterilization, shipping and storage.

Attaching surgical sutures to needles is well known in the art. Surgical needles and sutures have historically been attached by hand with a setup time between 20 and 30 minutes using a simple crimping die. The manual operators are typically able to do five to six parts per minute. This manual process has the suture and needle combination handed off to either a manual hand winding process, or the combination can be hand fed into an automatic winding machine. There are some attached swage wind combinations but these cannot be hand fed into an automatic winding machine. These swage wind combinations typically have expensive swage tools that can require up to 120 minutes for changeover and setup.

The machines currently in use for automatically attaching needles to suture are usually quite slow. Approximately, seven to ten parts can be attached per minute and the machines require 45 to 60 minutes to be set up. Automated equipment can require up to two hours for changeover.

There is a need in this art for a novel automated suture attaching process that overcomes the deficiencies of the prior art. Furthermore, there is a need in this art to shorten the changeover time from a large needle suture combination to a small needle suture combination.

SUMMARY

Proceeding from this previously known prior art, it is an object of the present invention to provide a novel suture winding machine with allows for automatically loading and winding micro needles and micro sutures and which can be easily adapted from automatically loading to manual loading in order to allow for faster winding of the suture.

Accordingly, a novel apparatus for attaching surgical sutures to needles and loading them into a winding machine is disclosed.

In the science of attaching the suture to the needle it is imperative that the centre of the needle and the centre of the suture are known. It is critical how the needle is held prior to the insertion of the suture into the hole in the end of the needle as each type of needle has a different outside diameter. Furthermore, the hole in the end of the needle might be based off the centre of that diameter.

The outside diameter of the suture has very little clearance for insertion and the outside diameter of the suture also changes with the size of the suture. Therefore, it is critical to know where the centre of the suture is. This is achieved by guiding the suture along the suture path using V grooved guides. The use of the V grooved guides is well known in the art. For the final guiding of the suture into the hole of the needle a very precise system is needed. It is possible to use a funnel which needs to be perfectly aligned with the needle and therefore also perfectly aligned with the crimping dies used to centre the needles.

The needle needs to be located in both the horizontal and the vertical position. The location of the horizontal position is controlled by the location tolerance on the crimping die. Therefore, this position is well repeatable when dies are changed out. The location of the vertical position is controlled by the height of the die. This position changes every time a die is reworked. So the upper and the lower die must be adjusted separately using hand tools like wrenches to move a screw up or down or to slowly close the dies separately until the centre is located. This type of setup using screw adjustment causes the need of readjustment over and over again. Therefore, the efficiency is low as the initial setup could take up to 60 minutes to complete. Therefore, a more efficient method of finding the centre of the dies regardless of the length of the needle was developed. Next we will describe the device that well enable the machine to automatically go to the vertical centre after new dies are installed.

The needle suture attaching station of this apparatus has a novel die setup arrangement. Most dies vary in height due to rework and it can take quite some time to offset this variance. Therefore, the present invention has a digital measuring station to measure the height of the die. The measurements can then be downloaded to the suture attaching station where it is normalized to a set zero point. Alternatively, the measurements can be manually entered at the HMI. This method reduces the setup time of the crimping die to a maximum of five minutes, keeping changeover to a minimum. This measuring station could be offline. The rest of the automatic crimping is well known in the art but the footprint has been reduced by simplifying the suture infeed process.

The interface between the suture attaching machine and the winding machine is a hand off to one of two infeed lines. One of the infeed lines is a straight motion to the winding machine with its robot grippers for gripping the needles and placing them into a needle park or a foam park of the tray. When this infeed line is not in use, the suture attaching machine offloads to a bin where the needle and suture combinations are stacked into bundles and can be manually offloaded. The second one of the infeed lines is at a 90-degree angle to allow for hand feeding of bundles needle and suture combinations. In this case, the sutures could have been hand crimped because of the small batch size or because they are a combination smaller than USP 5/0.

The infeed slides of the infeed lines allow for the manual placing of the needle to be transported to the pickup station of the winding machine. This is designed to accommodate single and double armed sutures down to 5/0 and single arm sutures below 5/0. With a quick change of the robot grippers it could also accommodate needles down to 8 millimetres to 8/0 sutures.

These and other features and advantages of the present invention will become more apparent from the following description and accompanying drawings.

Further advantages and features of the invention can be gathered from the features which are further specified in the claims and from the following exemplary embodiments.

BRIEF DESCRIPTION OF THE DRAWINGS

In the following text, the invention will be described and explained in greater detail using the exemplary embodiments which are shown in the drawings.

DETAILED DESCRIPTION

Figure 1:
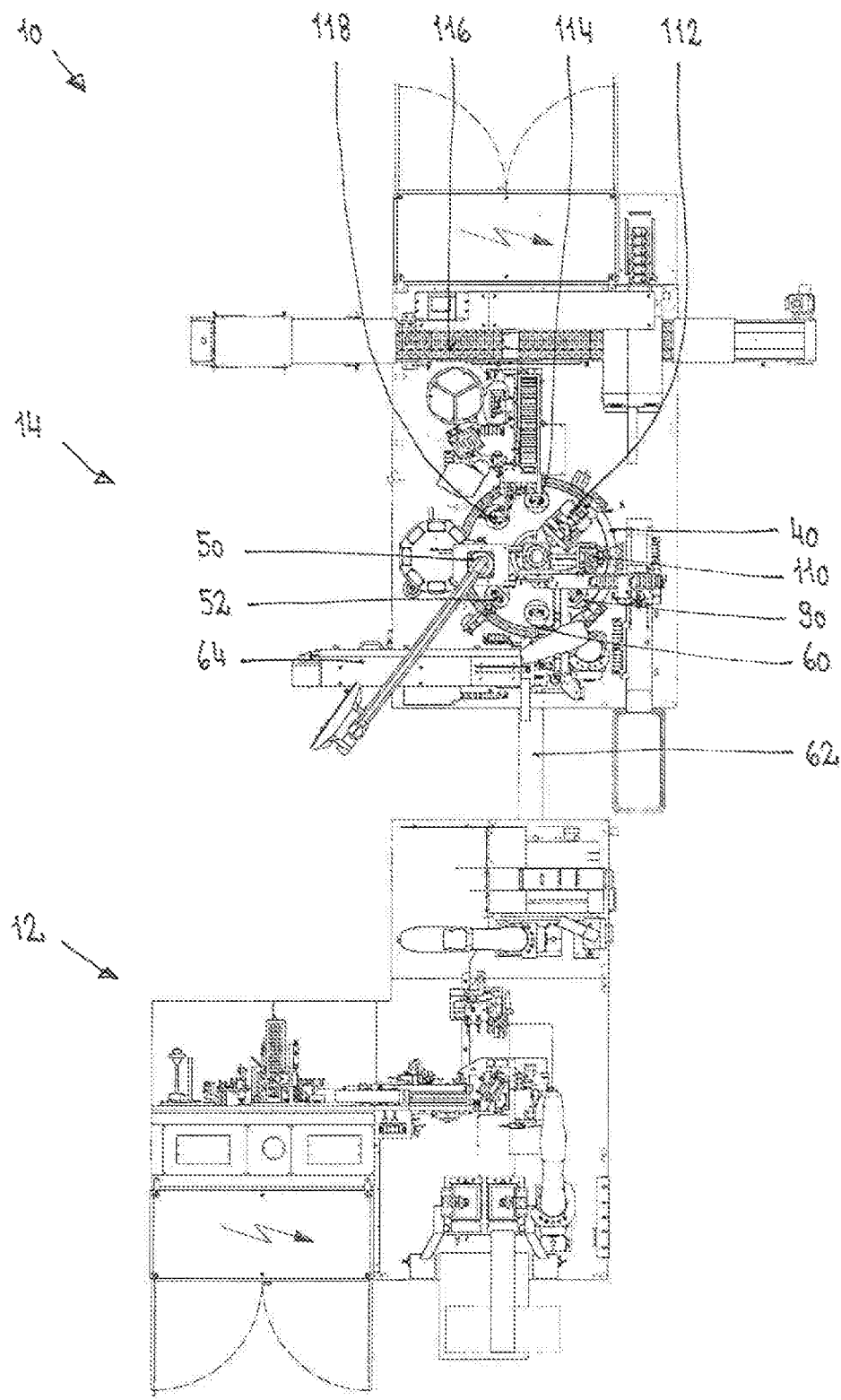
FIG. 1 is a schematic view of the winding machine with suture attaching machine.

The combined machine 10 according to FIG. 1 consists of two main units, the first unit being a suture attaching station 12 and the second unit being a winding machine 14.

Figure 2:
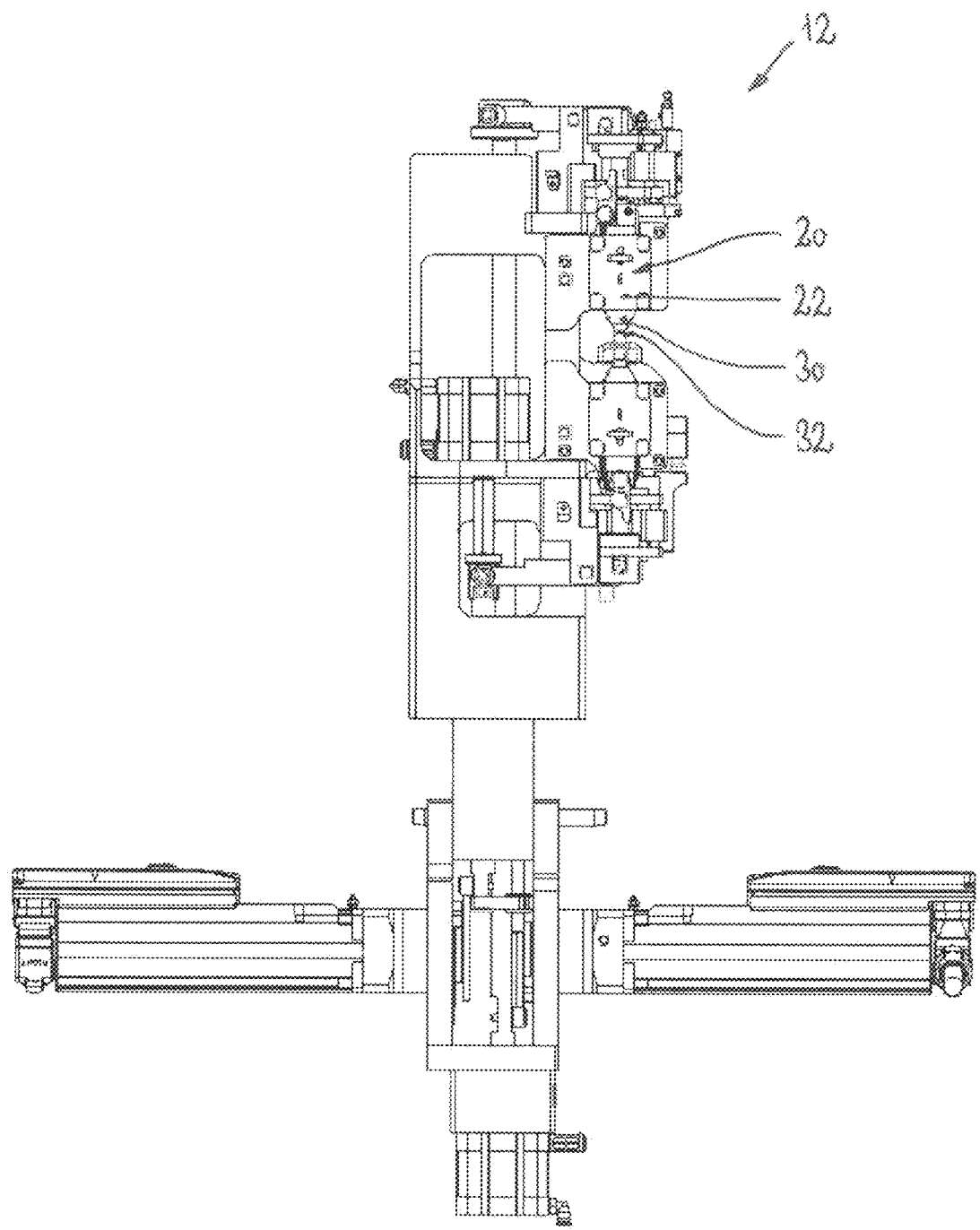
FIG. 2 is a schematic view of the suture attaching machine according to FIG. 1.
Figure 3:
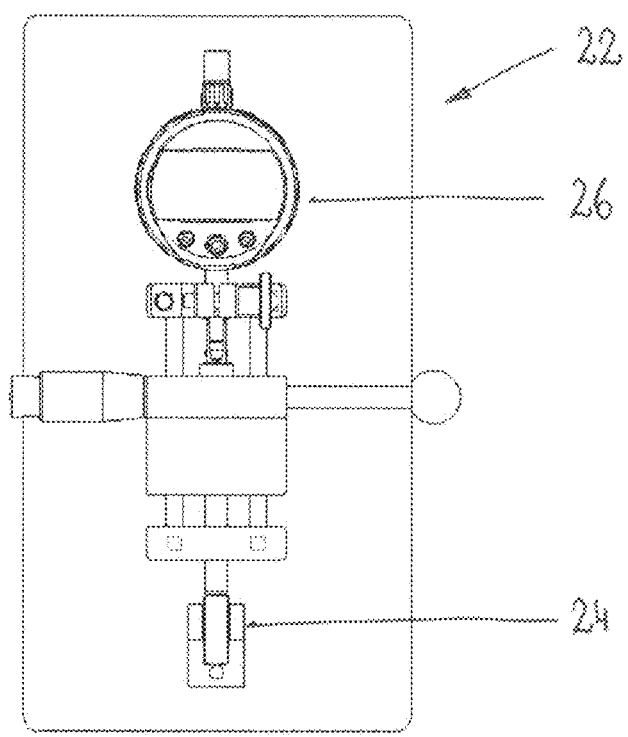
FIG. 3 is a schematic view of the offline measuring fixture of the suture attaching machine.

The suture attaching station 12 attaches the needle and suture to form a single combination. This station 12 is shown in greater detail in FIG. 2. The setup of the crimping unit 20 is facilitated by using an offline measuring fixture 22 which is shown in FIG. 3. The offline measuring fixture 22 is calibrated by placing a precision gage block 24 into the measuring fixture 22 and then zeroing the digital measuring unit 26. The gage block 24 is then replaced by the desired crimping die 30 and the reading is noted as an offset for the servo drive of the suture attaching station 12. This offset is used to set the zero point of the crimping die centre 32. This can be done manually via the HMI of the station or automatically when the measurement system is connected to the machine plc. The crimping dies usually have a top part and a bottom part.

The needle and suture combination is then transferred to the winding machine 14, which is preferred to be inline but can be at any angle. Referring to FIG. 1, the winding machine 14 has a base platform 40 with a rotary dial mounted thereon. In this preferred embodiment there are eight package nests on the rotary dial. Each of the package nests is labelled so it will be possible to track the trays during the winding process. There could be more than eight package nests or less than this, depending on the number of stations necessary for the winding process.

This type of rotary dial is widely used in the art so it is not described in detail. On the outside of the rotary dial is the base plate for mounting each of the stations. This modular design allows for quick customization of the stations as may be required by the design of the tray or by station requirements.

The first station 50 is the tray infeed. This station 50 is shown at nine o'clock of the rotary dial according to FIG. 1. This type of infeed station 50 is widely used in the art so it is not described in detail. In principal, there are two options. There could be a single stack of trays to be loaded into the package nests or there could be a multi stack carrousel. In both cases the trays are singularized and placed onto the package nests.

In the shown embodiment, the package nests are rotated in an anticlockwise direction. The second station 52 is an open station for further options. For example, this station 52 could be used to load a top of the tray. It would also be possible to cut and place a foam in this station 52. If micro-needles do not fit into the needle park of the tray, such a foam might be necessary.

In the third station 60 the needle with an attached suture is fed in and parked in the tray. The third station 60 comprises two infeed lines 62, 64. The infeed lines 62, 64 are positioned at 90-degree angle to each other. The primary infeed line 62 is used for the transfer from the suture attaching station 12 to the winding machine 14. The secondary infeed line 64 is used for manual loading of a needle when switched to stand alone mode.

The infeed slides of infeed line 62, 64 move to the pickup station of the third station 60. Infeed slides like this are widely used in the art so they are not described in detail. At the pickup station robot grippers grip the needles from the infeed slides. The slide then returns to its loading position. The robot grippers now travel to the package nest of the rotary dial and load the needle into a needle park of the tray.

The fourth station 90 is the winding station. This winding station 90 can wind trays with vacuum present or without vacuum present. If there is no vacuum present during the winding, it is usually necessary to have the lid placed directly after the needle parking and before starting the winding of the suture. Therefore, in this case the fifth station 110 together with the sixth station 112 should be placed after the third station 60 and before the winding station 90.

The fifth station 110 is a printing and lid placement station. The lids could be pre-printed paper lids of plastic lids or the like. This type of station 110 is widely used in the art so it is not described in detail.

The sixth station 112 is the lid attachment station. The lid could be attached by using ultrasonic sound or heated die, for example. By using ultrasonic sound or heated die it is possible to deform the standoff members of the trays, thereby locking the lid in place. This type of station 112 is widely used in the art so it is not described in detail.

The seventh station 114 is an offloading station. After offloading, the trays are usually transported to an intermediate inspection station (not shown). This type of station 114 is widely used in the art so it is not described in detail. The intermediate inspection station is usually the station where all camera inspections are performed. The tray is then transferred to an outfeed section 116 which can be a belt or a magazine, for example. It could also be transferred to a reject area. It can be advantageous to have a demagnetisation of the needle before offloading the tray.

This kind of intermediate inspection station is widely used in the art so it is not described in detail.

The eighth station 118 is an open station for further options. For example, this station 118 could be used for a camera check in order to confirm the offloading of the tray.

In contrast to the circular layout of the rotary dial 42, there could also be an inline form for the suture winding machine 14. It is also possible to have a combination of a rotary dial 42 and an inline form. The winding process of the present invention can be used with tray suture packages of various designs. The shape of the tray 14 can be essentially circular to oval. It can also be oval with finger indentations on the outer periphery (peanut shape).

What is claimed is:

1. An apparatus for attaching surgical sutures to needles, comprising:
   a crimping unit;
   an exchangeable crimping die; and
   a measuring fixture comprising a measuring unit to measure a dimensional height of the exchangeable crimping die and to measure a dimensional height of a precision gage block, said precision gage block being interchangeable with the exchangeable crimping die.

2. A method, comprising:
   providing the apparatus as in claim 1;
   calibrating the measuring unit with the precision gage block;
   measuring the dimensional height of the exchangeable crimping die as an offset to the precision gage block; and using the offset for setting a zero point of the center of the exchangeable crimping die.

* * * * *